United States Patent
Gifford et al.

(10) Patent No.: US 11,149,298 B2
(45) Date of Patent: Oct. 19, 2021

(54) DETECTION OF NUCLEIC ACID SEQUENCES USING DETERMINISTIC LATERAL DISPLACEMENT ARRAYS

(71) Applicant: International Business Machines Corporation, Armonk, NY (US)

(72) Inventors: Stacey Gifford, Fairfield, CT (US); Sung-Cheol Kim, New York, NY (US); Joshua T. Smith, Croton on Hudson, NY (US); Benjamin Wunsch, Mt. Kisco, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 311 days.

(21) Appl. No.: 16/007,347

(22) Filed: Jun. 13, 2018

(65) Prior Publication Data
US 2019/0382828 A1    Dec. 19, 2019

(51) Int. Cl.
| | | |
|---|---|---|
| *G01N 15/02* | (2006.01) | |
| *C12Q 1/6813* | (2018.01) | |
| *C12Q 1/6806* | (2018.01) | |
| *C12Q 1/6825* | (2018.01) | |
| *G01N 15/10* | (2006.01) | |

(52) U.S. Cl.
CPC ......... *C12Q 1/6813* (2013.01); *C12Q 1/6806* (2013.01); *C12Q 1/6825* (2013.01); *G01N 15/02* (2013.01); *G01N 15/1056* (2013.01); *B01L 2400/086* (2013.01)

(58) Field of Classification Search
None
See application file for complete search history.

(56) References Cited

U.S. PATENT DOCUMENTS

| | | |
|---|---|---|
| 6,403,338 B1 | 6/2002 | Knapp et al. |
| 6,955,874 B2 | 10/2005 | Singh et al. |
| 7,745,119 B2 | 6/2010 | Koshinsky et al. |

(Continued)

FOREIGN PATENT DOCUMENTS

| | | |
|---|---|---|
| CA | 2049429 A1 | 2/1992 |
| CN | 105019033 A | 11/2015 |

(Continued)

OTHER PUBLICATIONS

Kaji et al, Anal. Chem, vol. 76, pp. 15-22, published online Nov. 26, 2003.*

(Continued)

*Primary Examiner* — Robert T. Crow
(74) *Attorney, Agent, or Firm* — Amin, Turocy & Watson, LLP

(57) ABSTRACT

Techniques regarding detecting one or more defined nucleic acid sequences are provided. For example, one or more embodiments described herein can comprise a method, which can comprise adding a molecular probe to a sample fluid comprising a first deoxyribonucleic acid segment and a second deoxyribonucleic acid segment. The molecular probe can have an affinity to bond to a defined nucleic acid sequence. The method can also comprise separating, via a nanoscale deterministic lateral displacement array, the first deoxyribonucleic acid segment from the second deoxyribonucleic acid segment based on a size of the first deoxyribonucleic acid segment.

20 Claims, 12 Drawing Sheets

(56) References Cited

U.S. PATENT DOCUMENTS

| | | | |
|---|---|---|---|
| 7,906,287 | B2 | 3/2011 | Dahlhauser |
| 8,323,929 | B2 | 12/2012 | Wang et al. |
| 8,796,506 | B2 | 8/2014 | Gielen et al. |
| 8,975,216 | B2 | 3/2015 | Rank et al. |
| 9,559,240 | B1 | 1/2017 | Astier et al. |
| 10,253,350 | B2* | 4/2019 | Gifford .............. B01L 3/502761 |
| 2001/0014449 | A1 | 8/2001 | Nerenberg et al. |
| 2004/0072247 | A1 | 4/2004 | Pfistershammer |
| 2008/0023399 | A1* | 1/2008 | Inglis ............... G01N 33/54366 210/649 |
| 2012/0220479 | A1* | 8/2012 | Ericsson .............. C12Q 1/6855 506/9 |
| 2014/0155271 | A1 | 6/2014 | Hatchwell et al. |
| 2015/0136601 | A1* | 5/2015 | Austin ................... B82Y 30/00 204/451 |
| 2015/0368706 | A1 | 12/2015 | Cao et al. |
| 2016/0047735 | A1* | 2/2016 | Grisham ........... B01L 3/502776 435/7.1 |
| 2016/0146778 | A1* | 5/2016 | Astier ................ G01N 27/3278 506/12 |
| 2016/0320389 | A1* | 11/2016 | Astier .............. G01N 33/56983 |
| 2017/0035734 | A1 | 2/2017 | Bray et al. |
| 2017/0342477 | A1 | 11/2017 | Jensen et al. |

FOREIGN PATENT DOCUMENTS

| | | | |
|---|---|---|---|
| JP | 2007061080 | A | 3/2007 |
| WO | 2011047359 | A2 | 4/2011 |
| WO | 2013154770 | A1 | 10/2013 |

OTHER PUBLICATIONS

Inglis, et al., Critical particle size for fractionation by deterministic lateral displacement, Lab on a Chip, 2006, pp. 655-658, vol. 6.

Wunsch, et al., Nanoscale lateral displacement arrays for the separation of exosomes and colloids down to 20 nm, Nature Nanotechnology, Aug. 1, 2016, 7 Pages.

List of IBM Patents or Applications Treated as Related.

Smith, et al. "Microfluidic Chips With One or More Vias Filled With Sacrificial Plugs." U.S. Appl. No. 16/168,292, filed Oct. 23, 2018. 37 pages.

Non-Final Office Action received for U.S. Appl. No. 16/007,389 dated Aug. 4, 2020, 89 pages.

Gao et al, "Sequence-dependent cleavage of mismatched DNA by Ban I restriction endonuclease"vol. 30, article e2638, Mar. 21, 2017, 11 pages.

Ishino et al., "NAR Breakthrough Article Identification of a mismatch—specific endonuclease in hyperthermophilic Archaea", Nucleic Acids Research, vol. 44, No. 7, pp. 2977-2986.

Pimkin et al., "Recombinant nucleases CEL I from celery and SP I from spinach for mutation detection", BMC Biotechnology vol. 7, Article 29, 2007, pp. 1-8.

Brow et al., "Mutation Detection by Cleavase® Fragment Length Polymorphism Analysis", Focus, vol. 18, 1996, pp. 2-5.

Grompe et al., "Scanning detection of mutations in human ornithine transcarbamoylase by chemical mismatch cleavage", Proc. Nat. Acad. Sci. USA, vol. 86, Aug. 1989, pp. 5888-5892.

Cotton et al, "Reactivity of cytosine and thymine in single-base-pair mismatches with hydroxylamine and osmium tetroxide and its application to the study of mutations", Proc. Nat. Acad. Sci. USA, vol. 85, Jun. 1988, pp. 4397-4401.

Final Office Action received for U.S. Appl. No. 16/007,389 dated Nov. 20, 2020, 77 pages.

Kojima et al.,"Hydroxylamine, oxime and hydroxamic acid derivatives of nucleic acids", PAT AI's Chemistry of Functional Groups, 2010, 45 pages.

Non-Final Office Action received for U.S. Appl. No. 16/007,389 dated Mar. 12, 2021, 43 pages.

* cited by examiner

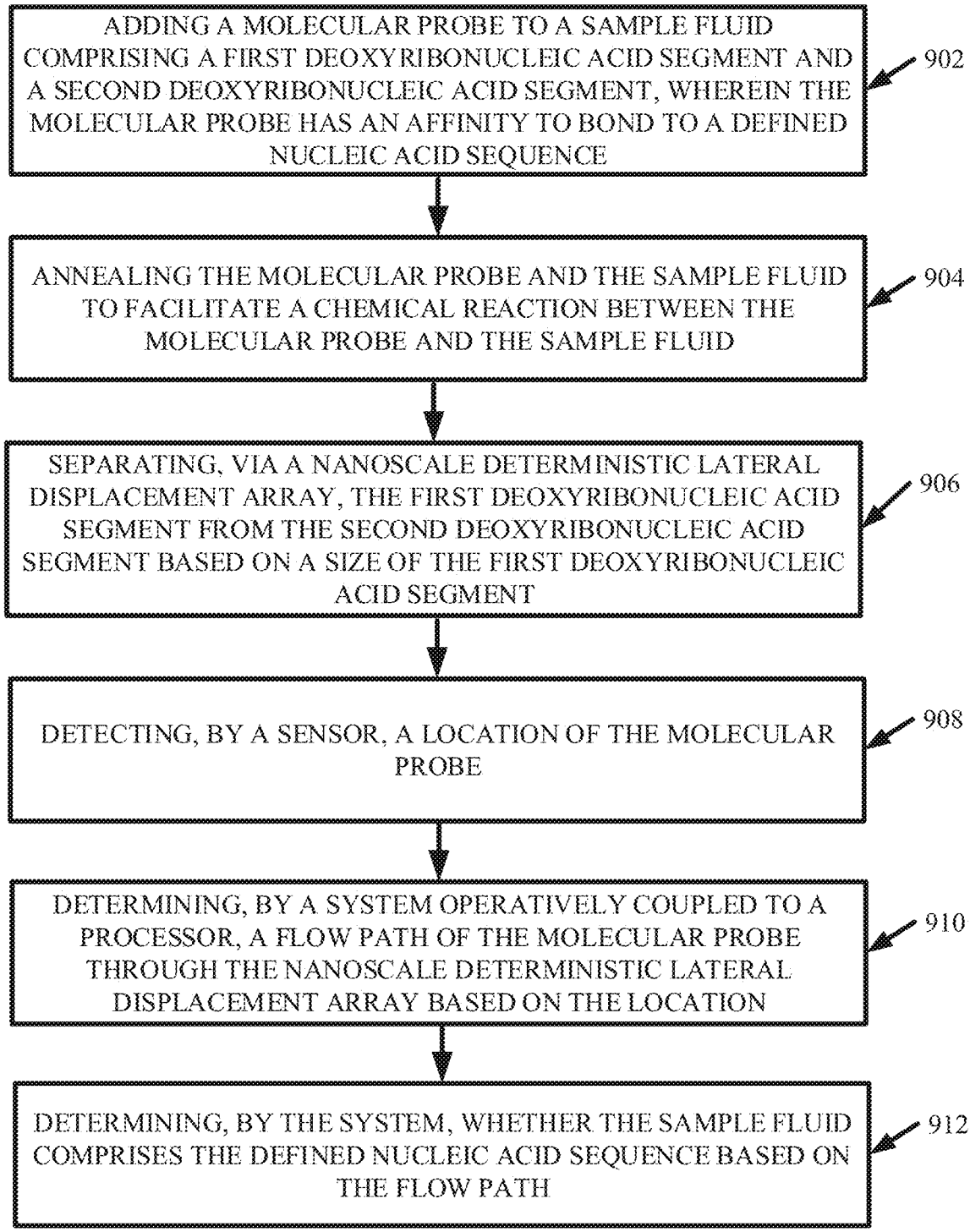

```
┌─────────────────────────────────────────────────────────┐
│  ANNEALING A SAMPLE FLUID COMPRISING A PROBE            │
│  MOLECULE, A FIRST DEOXYRIBONUCLEIC ACID SEGMENT, AND   │──1002
│  A SECOND DEOXYRIBONUCLEIC ACID SEGMENT, WHEREIN THE    │
│  PROBE MOLECULE BONDS TO THE FIRST DEOXYRIBONUCLEIC     │
│  ACID SEGMENT BASED ON THE FIRST DEOXYRIBONUCLEIC       │
│  ACID SEGMENT COMPRISING A DEFINED NUCLEIC ACID         │
│  SEQUENCE                                               │
└─────────────────────────────────────────────────────────┘
                              │
                              ▼
┌─────────────────────────────────────────────────────────┐
│  SEPARATING, VIA A NANOSCALE DETERMINISTIC LATERAL      │
│  DISPLACEMENT ARRAY, THE FIRST DEOXYRIBONUCLEIC ACID    │──1004
│  SEGMENT FROM THE SECOND DEOXYRIBONUCLEIC ACID          │
│  SEGMENT BASED ON A SIZE OF THE FIRST DEOXYRIBONUCLEIC  │
│  ACID SEGMENT                                           │
└─────────────────────────────────────────────────────────┘
```

ADDING A MOLECULAR PROBE TO A SAMPLE FLUID COMPRISING A DEOXYRIBONUCLEIC ACID SEGMENT, WHEREIN THE MOLECULAR PROBE HAS AN AFFINITY TO BOND TO A DEFINED NUCLEIC ACID SEQUENCE — 1102

DISPLACING, VIA A NANOSCALE DETERMINISTIC LATERAL DISPLACEMENT ARRAY COMPRISED WITHIN A MICROFLUIDIC CHANNEL, THE DEOXYRIBONUCLEIC ACID SEGMENT TOWARDS A COLLECTION REGION OF THE MICROFLUIDIC CHANNEL, WHEREIN THE NANOSCALE DETERMINISTIC LATERAL DISPLACEMENT ARRAY DISPLACES A MOLECULE HAVING A SIZE GREATER THAN A DEFINED THRESHOLD, AND WHEREIN A SIZE OF THE MOLECULAR PROBE IS LESS THAN THE DEFINED THRESHOLD — 1104

DETECTION OF NUCLEIC ACID SEQUENCES USING DETERMINISTIC LATERAL DISPLACEMENT ARRAYS

BACKGROUND

The subject disclosure relates to utilizing one or more deterministic lateral displacement arrays to detect one or more nucleic acid sequences, and more specifically, to utilizing one or more deterministic lateral displacement arrays to determine whether one or samples comprise one or more target nucleic acid sequences.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, apparatuses, and/or methods that can regard detecting one or more target deoxyribonucleic acid sequences via one or more deterministic lateral displacement arrays are described.

According to an embodiment, a method is provided. The method can comprise adding a molecular probe to a sample fluid comprising a first deoxyribonucleic acid segment and a second deoxyribonucleic acid segment. The molecular probe can have an affinity to bond to a defined nucleic acid sequence. The method can also comprise separating, via a nanoscale deterministic lateral displacement array, the first deoxyribonucleic acid segment from the second deoxyribonucleic acid segment based on a size of the first deoxyribonucleic acid segment.

According to another embodiment, another method is provided. The method can comprise annealing a sample fluid comprising a probe molecule, a first deoxyribonucleic acid segment, and a second deoxyribonucleic acid segment. The probe molecule can bond to the first deoxyribonucleic acid segment based on the first deoxyribonucleic acid segment comprising a defined nucleic acid sequence. The method can also comprise separating, via a nanoscale deterministic lateral displacement array, the first deoxyribonucleic acid segment from the second deoxyribonucleic acid segment based on a size of the first deoxyribonucleic acid segment.

According to another embodiment, another method is provided. The method can comprise adding a molecular probe to a sample fluid comprising a deoxyribonucleic acid segment. The molecular probe can have an affinity to bond to a defined nucleic acid sequence. The method can also comprise displacing, via a nano scale deterministic lateral displacement array comprised within a microfluidic channel, the deoxyribonucleic acid segment towards a collection region of the microfluidic channel. The nanoscale deterministic lateral displacement array can displace a molecule having a size greater than a defined threshold. Also, a size of the molecular probe can be less than the defined threshold.

BRIEF DESCRIPTION OF THE DRAWINGS

FIG. 9 illustrates a flow diagram of an example, non-limiting method that can facilitate detecting whether one or more target deoxyribonucleic acid sequences are present in a fluid sample in accordance with one or more embodiments described herein.

FIG. 10 illustrates a flow diagram of an example, non-limiting method that can facilitate detecting whether one or more target deoxyribonucleic acid sequences are present in a fluid sample in accordance with one or more embodiments described herein.

FIG. 11 illustrates a flow diagram of an example, non-limiting method that can facilitate detecting whether one or more target deoxyribonucleic acid sequences are present in a fluid sample in accordance with one or more embodiments described herein.

DETAILED DESCRIPTION

Figure 1:
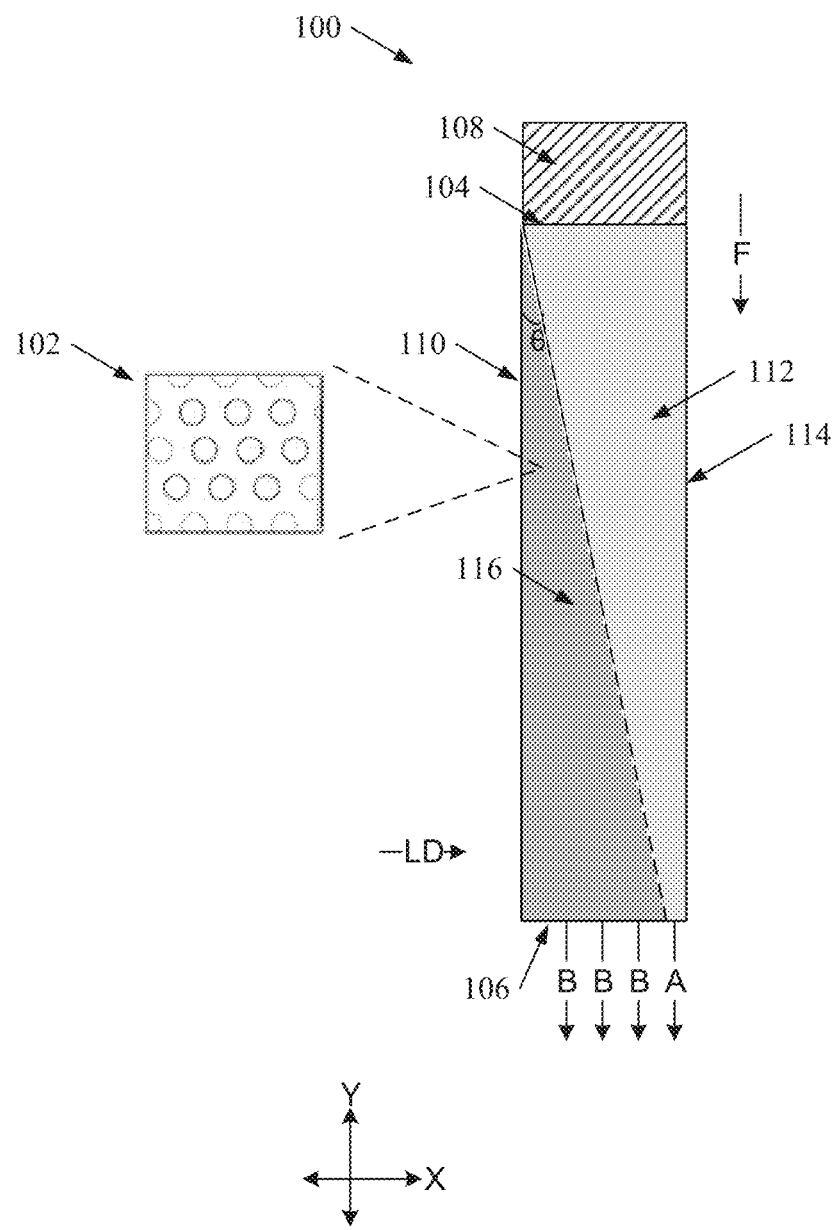
FIG. 1 illustrates a diagram of an example, non-limiting microfluidic channel that can comprise one or more deterministic lateral displacement arrays, which can separate deoxyribonucleic acid sequences based on size in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details. Further, it is to be understood that common cross-hatching and/or shading depicted across the drawings can represent common features, compositions, and/or conditions described herein in accordance with one or more embodiments.

Genetic code is the underlying source of thousands of inheritable diseases and/or traits for individuals, animals, plants, bacteria, viruses, and/or the like. Said genetic code comprises deoxyribonucleic acid ("DNA") sequences and ribonucleic acid ("RNA") sequences. Detecting DNA and RNA sequences can facilitate identify diseases, traits, health conditions, and/or physical properties associated with an entity (e.g., individuals, animals, plants, bacteria, viruses, and/or the like). For example, the presence of particular DNA and/or RNA sequences can be indicative of one or more diseases such as cystic fibrosis, which stem from specific point mutations, as well as heart disease, which can have increased risk associated with a combination of specific genetic sequences. In another example, other traits such as fetal development and/or colorblindness can be detected by the presence of specific genetic sequences.

Current methods for genetic sequence (e.g., DNA sequence) detection rely on amplification techniques such as polymerase chain reactions ("PCR") and DNA sequencing technologies. PCR techniques can amplify one or more target DNA sequences across multiple orders of magnitude, thereby generating thousands to millions of copies of the target DNA sequence. However, PCR techniques necessitate intricate steps, specialized equipment, laboratory facilities, and/or undesirable lengths of time.

Various embodiments described herein can regard rapid single molecule detection that can detect target genetic sequences substantially faster than conventional techniques. Further, one or more embodiments can utilize microfluidics in a lab-on-a-chip device to detect one or more target genetic sequences via deterministic lateral displacement (e.g., one or more nanoscale deterministic lateral displacement arrays). For example, one or more embodiments can detect whether one or more target genetic code sequences are comprised within a sample, wherein the target genetic code sequences can be indicative of various traits (e.g., physical properties) and/or health conditions (e.g., diseases). Thus, one or more embodiments described herein can regard one or more LOC devices that can facilitate genetic code sequence detection, wherein the one or more LOC devices can be operated quickly (e.g., near instantaneously), in a variety of locations (e.g., at an entity's home), and without the typical need for specialized laboratory equipment.

As used herein, the term "lab-on-a-chip ("LOC")" can refer to one or more devices that can integrate one or more laboratory functions onto an integrated circuit (e.g., a semiconductor substrate structure) to achieve autonomous screening of one or more samples. LOCs can utilize microelectromechanical systems and/or microfluidic systems to facilitate screening the one or more samples. One of ordinary skill in the art will recognize that a LOC devices can range in size from, for example, one or more square millimeters to one or more square centimeters.

As used herein the term "deterministic lateral displacement ("DLD")" can refer to one or more microfluidic techniques that can size fractionate a polydisperse suspension of molecules through the use of one or more arrays of obstacles. For example, DLD arrays can laterally displace target molecules within a sample stream based on size. Further, DLD arrays can comprise a plurality of pillars arranged in a lattice structure. Rows of pillars comprising the lattice structure can be positioned offset of each other at a defined angle, and pillars can be separated from each other by a defined gap size. The defined angle and/or gap size can facilitate displacement of one or more molecules of a target size range comprised within a stream flowing through the DLD array.

As used herein the term "nano-DLD array" can refer to a DLD array that can be characterized by one or more dimensions ranging from greater than or equal to 1 nanometer (nm) and less than or equal to 999 nm. For example, a nano-DLD array can be a DLD array characterized by a gap size (e.g., a distance between adjacent pillars comprised within the lattice structure) of greater than or equal to 1 nm and less than or equal to 999 nm (e.g., greater than or equal to 25 nm and less than or equal to 235 nm). In one or more embodiments, a nano-DLD array can facilitate displacement of genetic code sequences that can be characterized as having an exemplary length ranging from, but not limited to, greater than or equal to 25 base pairs (bp) and less than or equal to 200 bp.

FIG. 1 illustrates a diagram of an example, non-limiting microfluidic channel 100 that can comprise one or more nano-DLD arrays 102, which can facilitate lateral displacement of one or more molecules based on size in accordance with one or more embodiments described herein. The microfluidic channel 100 can comprise one or more inlets 104 and/or one or more outlets 106. One or more sample fluids 108 can enter the microfluidic channel 100 via the one or more inlets 104 and flow through the one or more nano-DLD arrays 102 (e.g., in a flow direction represented by the "F" arrow in FIG. 1) to exit the microfluidic channel 100 via the one or more outlets 106. FIG. 1 depicts a full-width injection configuration of the microfluidic channel 100 in which the one or more sample fluids 108 can enter the microfluidic channel 100 across the entire, and/or nearly the entire, width (e.g., along the "X" direction) of the microfluidic channel 100.

The one or more nano-DLD arrays 102 can comprise a lattice of asymmetric pillars arranged in rows and/or columns. FIG. 1 shows an expanded view (e.g., as indicated by dashed lines) of a portion of the one or more nano-DLD arrays 102 to illustrate an exemplary structure. As shown in the expanded portion, the plurality of pillars comprised within the one or more nano-DLD arrays 102 can be arranged at an angle (e.g., represented by "θ" in FIG. 1) with respect to one or more side walls 110 of the microfluidic channel 100, such that one or more rows and/or columns of the pillars can be offset from adjacent rows and/or columns of the pillars. For example, the angle (e.g., represented by "θ") can be greater than or equal to 0 degrees and less than or equal to 90 degrees. The one or more nano-DLD arrays 102 can extend across a portion and/or an entirety of the width (e.g., along the "X" direction) of the microfluidic channel 100. Also, the one or more nano-DLD arrays 102 can extend across a portion and/or an entirety of the length (e.g., along the "Y" direction) of the microfluidic channel 100. Further, the one or more nano-DLD arrays 102 can have a uniform gap size between pillars along the width (e.g., along the "X" direction) and/or length (e.g., along the "Y" direction) of the microfluidic channel 100. Alternatively, the one or more nano-DLD arrays 102 can have varying gap sizes between pillars along the width (e.g., along the "X" direction) and/or length (e.g., along the "Y" direction) of the microfluidic channel 100. For example, the gap size of the one or more nano-DLD arrays 102 can decrease (e.g., gradually and/or abruptly) along the length (e.g., along the "Y" direction) of the microfluidic channel 100.

The one or more sample fluids 108 can comprise one or more genetic code sequences. Further, the one or more sample fluids 108 can include, but are not limited to: in vitro samples, plant samples, food samples, blood samples, urine samples, tissue samples, saliva samples, a combination thereof, and/or the like. For example, the one or more sample fluids 108 can comprise, but are not limited to: DNA from clinical samples, isolated genomic DNA, purified DNA, a combination thereof, and/or the like. In various embodiments, the one or more sample fluids 108 can comprise DNA fragments and/or sequences of various sizes. For instance, the one or more sample fluids 108 can comprise DNA fragments and/or sequences having a size less than a critical diameter and DNA fragments and/or sequences having a size greater than or equal to the critical diameter. In another instance, the one or more sample fluids 108 can comprise DNA fragments and/or sequences having a size greater than or equal to a critical diameter. As used herein, the term "critical diameter" can refer to a defined threshold that can characterize a size at which molecules are subject to displacement (e.g., lateral displacement) by a subject nano-DLD array 102. In other words, molecules having a size greater than or equal to the critical diameter of a subject nano-DLD array 102 can be displaced towards a collection region by the nano-DLD array 102. The critical diameter of one or more nano-DLD arrays 102 can be affected by one or more dimensions of the nano-DLD arrays 102, such as gap size and/or the offset angle (e.g., represented by "θ").

For example, FIG. 1 can depict one or more sample fluids 108 that can comprise one or more first DNA segments and/or one or more second DNA segments. As the DNA segments flow through the one or more nano-DLD arrays 102 (e.g., in the flow direction represented by arrow "F"), respective DNA segments can experience different flow paths based on the size of the molecules. In other words, the one or more nano-DLD arrays 102 can separate the one or more first DNA segments from one or more of the second DNA segments.

Wherein the one or more first DNA segments can be larger than the critical diameter of the one or more nano-DLD arrays 102, the one or more first DNA segments can follow a first flow path 112. As shown by the first flow path 112 in FIG. 1, the one or more first DNA segments can be laterally displaced (e.g., in a lateral displacement direction represented by the "LD" arrow) towards a collection region (e.g., a collection wall 114 and/or a collection channel). For example, the one or more first DNA segments can be laterally displaced towards a collection wall 114 of the microfluidic channel 100. As the one or more first DNA segments flow through the one or more nano-DLD arrays 102, the one or more first DNA segments can be further displaced towards and/or concentrated adjacent to the collection wall 114. Thus, the one or more first DNA segments can exit the microfluidic channel 100 via the one or more outlets 106 as a concentrated stream (e.g., as represented by arrow "A"). Therefore, the one or more first DNA segments, being larger than the critical diameter of the one or more nano-DLD arrays 102, can be bumped (e.g., laterally displaced) towards a collection wall 114 to form a concentrated stream.

Wherein the one or more second DNA segments can be smaller than the critical diameter of the one or more nano-DLD arrays 102, the one or more second DNA segments can follow a second flow path 116. The one or more second DNA segments can zig-zag around the plurality of pillars within the nano-DLD array 102, thereby avoiding persistent lateral displacement towards the collection wall 114. Since the one or more sample fluids 108 can enter the one or more inlets 104 across the entire, or nearly the entire, width (e.g., along the "X" direction) of the microfluidic channel 100, the one or more second DNA segments can also enter the one or more inlets 104 across the entire, or nearly the entire, width (e.g., along the "X" direction) of the microfluidic channel 100; thus, the second flow path 116 of the one or more second DNA segments can overlap with the first flow path 112 (e.g., as indicated by a dashed line separating the first flow path 112 and/or the second flow path 116 in FIG. 1). Therefore, the one or more second DNA segments can exit (e.g., via the one or more outlets 106) the microfluidic channel 100 via a stream (e.g., represented by the plurality of "B" arrows) that can extend across the width of the microfluidic channel 100 and/or within the concentrated stream (e.g., represented by arrow "A") of the one or more first DNA segments.

Therefore, the one or more first DNA segments can be separated from one or more second DNA segments (e.g., one or more second DNA segments flowing along the left side of the microfluidic channel 100 shown in FIG. 1) while remaining adjacent to one or more other second DNA segments (e.g., one or more second DNA segments flowing along the right side of the microfluidic channel 100 shown in FIG. 1). By forming a concentrated stream (e.g., represented by the first flow path 112 and/or arrow "A"), the one or more nano-DLD arrays 102 can facilitate detection of the one or more first DNA segments.

Figure 2:
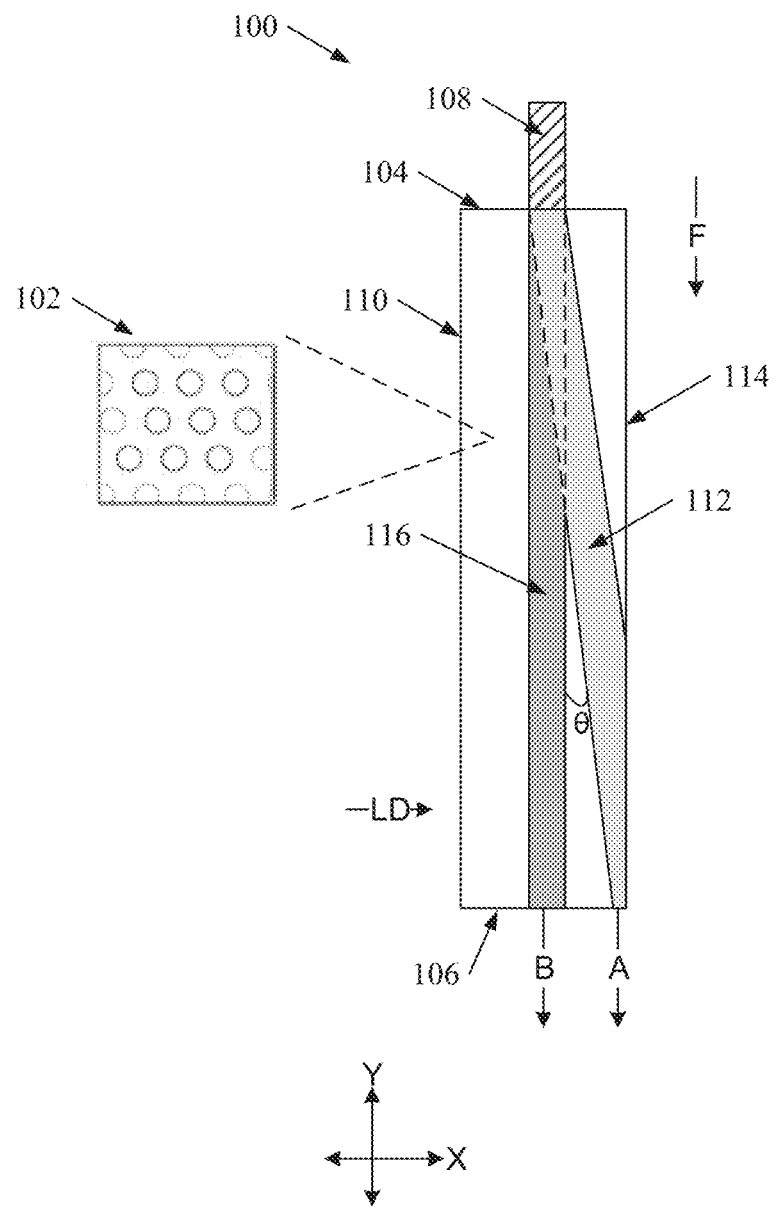
FIG. 2 illustrates a diagram of an example, non-limiting microfluidic channel that can comprise one or more deterministic lateral displacement arrays, which can separate deoxyribonucleic acid sequences based on size in accordance with one or more embodiments described herein.

FIG. 2 illustrates a diagram of the example, non-limiting microfluidic channel 100 that can comprise one or more nano-DLD arrays 102, which can facilitate lateral displacement of one or more molecules based on size in accordance with one or more embodiments described herein. Repetitive description of like elements employed in other embodiments described herein is omitted for sake of brevity. FIG. 2 depicts a focused injection configuration of the microfluidic channel 100 in which the one or more sample fluids 108 can enter the microfluidic channel 100 in a focused region of the microfluidic channel's 100 width (e.g., along the "X" direction).

As shown in FIG. 2, a focused injection configuration can comprise supplying the one or more sample fluids 108 to a defined region along the width (e.g., along the "X" direction) of the microfluidic channel 100. While FIG. 2 depicts the defined region within the center of the microfluidic channel's 100 width, the architecture of the microfluidic channel 100 is not so limited. For example, the defined region can be closer to the one or more side walls 110 than depicted in FIG. 2. The focused injection configuration of FIG. 2 can minimize overlap (e.g., as indicated by dashed lines) between the first flow path 112 and the second flow path 116, as compared to the overlap experienced with the full-width injection configuration depicted in FIG. 1.

Further, the focused injection configuration can result in two separate and distinct streams of molecules. For example, as described with regards to FIG. 1, the one or more nano-DLD arrays 102 can displace one or more first molecules (e.g., one or more first DNA segments) towards a collection region (e.g., collection wall 114 and/or a collection channel) in a lateral displacement direction (e.g., represented by arrow "LD"), thereby forming a concentrated stream of the first molecules exiting the one or more outlets 106 (e.g., represented by arrow "A"). Further, one or more second molecules (e.g., one or more second DNA segments) can flow through the one or more nano-DLD arrays 102 with minimal lateral displacement, thereby forming a distinct second stream (e.g., represented by arrow "B") comprising the one or more second molecules and separate from the first stream. Due to separation between the first stream and second stream (e.g., lack of overlap at the one or more outlets 106), detection of the one or more first molecules can be enhanced due to decreased contamination of the first stream by one or more second molecules.

Figure 3:
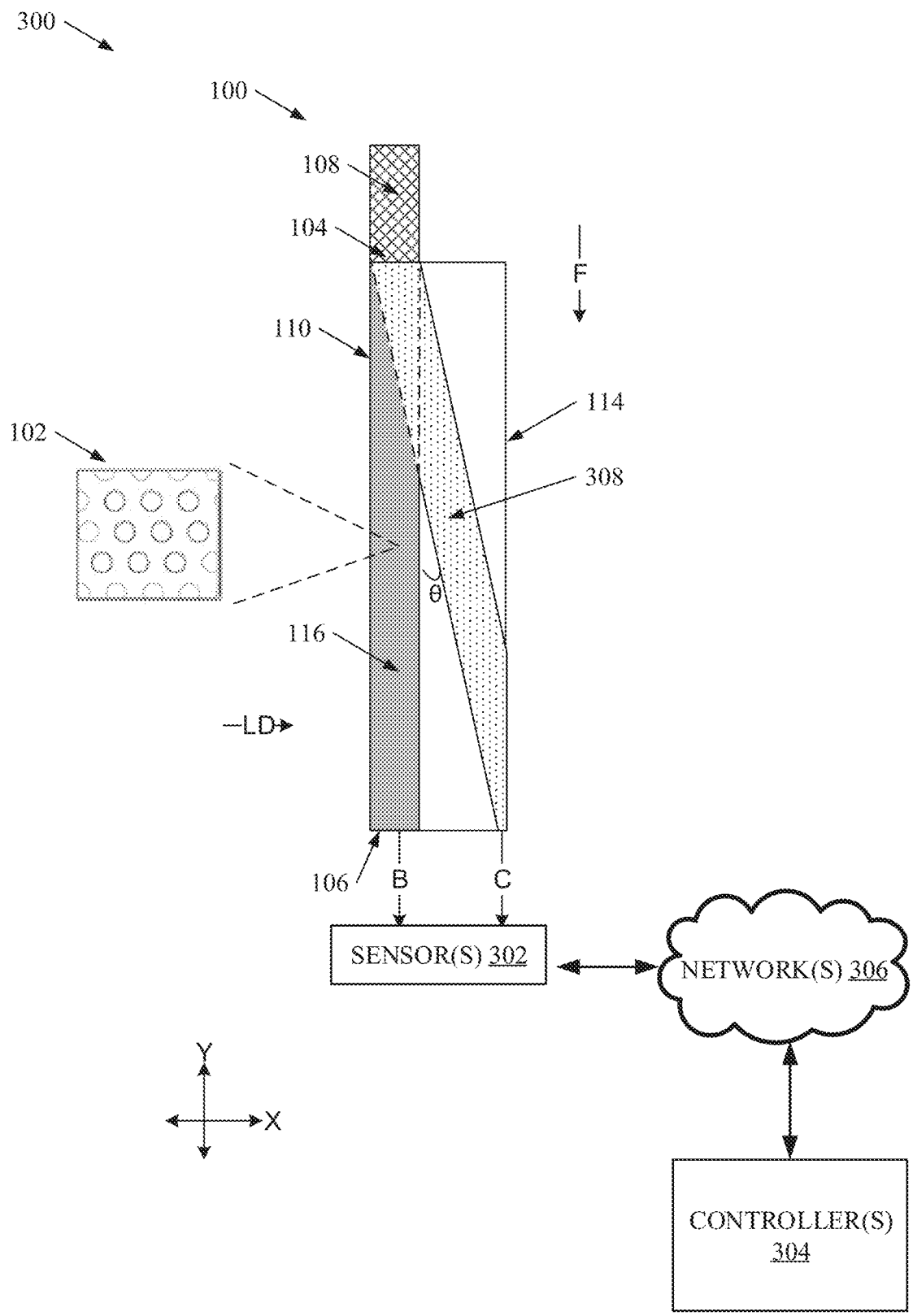
FIG. 3 illustrates a diagram of an example, non-limiting system that can comprise a microfluidic channel and can comprise facilitate detecting one or more defined nucleic acid sequences in accordance with one or more embodiments described herein.

FIG. 3 illustrates a diagram of the example, non-limiting system 300 that can comprise the microfluidic channel 100 and can facilitate detection of one or more molecular probes comprised within the one or more sample fluids 108 in accordance with one or more embodiments described herein. Repetitive description of like elements employed in other embodiments described herein is omitted for sake of brevity. As shown in FIG. 3, in various embodiments the system 300, for example the microfluidic channel 100, can comprise one or more sensors 302, which can be connected to one or more controllers 304 via one or more networks 306.

In one or more embodiments, the one or more sample fluids 108 can comprise one or more molecular probes in addition to one or more genetic code sequences (e.g., DNA segments). The one or more molecular probes can be characterized as molecules that have an affinity to bond (e.g., covalently bod) to a defined nucleic acid sequence. For example, the one or more molecular probes can comprise one or more nucleic acid sequences that are complimentary to one or more target DNA sequences. In one or more embodiments, the one or more molecular probes can have an affinity to anneal to a common target DNA segment. Additionally, in one or more embodiments the one or more sample fluids 108 can comprise a plurality of molecular probes. For example, one or more first molecular probes have an affinity to anneal to a first DNA segment while one or more second molecular probes have an affinity to anneal to a second DNA segment (e.g., wherein the first DNA segment comprises a different target nucleic acid sequence than the second DNA segment). Additionally, the number of nucleic acid sequences targeted by a plurality of molecular probes is not limited to two, in various embodiments the one or more sample fluids 108 can comprise a plurality of molecular probes with a cumulative affinity to anneal to three or more nucleic acid sequences.

Furthermore, the molecular probes can be smaller than the one or more critical diameters of the one or more nano-DLD arrays 102 comprised within the microfluidic channel 100. For example, a size of the one or more molecular probes can range from, but is not limited to, greater than or equal to 25 bp and less than or equal to 200 bp. One or more users of the microfluidic channel 100 can select molecular probe sizes based on, for example, the critical diameter of the one or more nano-DLD arrays 102. Additionally, the one or more molecular probes can be labelled to facilitate detection of the one or more molecular probes as they enter, traverse, and/or exit the microfluidic channel 100. For example, the one or more molecular probes can exit the one or more outlets 106 at one or more locations depending on the one or more molecular probes' interaction with the one or more nano-DLD arrays 102 (e.g., whether the one or more molecular probes are bumped towards a collection region or zig-zag through the one or more nano-DLD arrays 102).

In one or more embodiments, the one or more molecular probes can be labeled with one or more fluorescent tags (e.g., natural and/or synthetic fluorescent tags) to render the one or more molecular probes fluorescent and/or more readily identified by optical detection techniques. The one or more fluorescent tags can be, for example, bonded to the respective molecular backbones of the one or more molecular probes. Example fluorescent labeling techniques that can facilitate detection of the one or more molecular probes can include, but are not limited to: enzymatic labeling, chemical labeling, protein labeling, genetic labeling, DNA intercalating agents, a combination thereof, and/or the like. One of ordinary skill in the art will recognize that a variety of known fluorescent labelling techniques can be utilized to label the one or more molecular probes for detection by one or more sensors 302.

Further, in various embodiments, the one or more molecular probes can be labelled using one or more magnetic beads to render the one or more molecular probes more readily identified by electrical detection techniques. Example magnetic bead surface chemistries can include, but are not limited to: silica, oligo, specific oligonucleotide sequences, and/or the like. The one or more magnetic beads can be bonded to the one or more molecular probes to facilitate detecting the one or more molecular probes through triggered electrical shifts. One of ordinary skill in the art will recognize that a variety of known magnetic and/or electrochemical techniques can be used to render the one or more molecular probes readily identifiable by one or more sensors 302.

In one or more embodiments, the one or more sample fluids 108 can be prepared by facilitating potential hybridization reactions between the one or more molecular probes and/or the one or more genetic code sequences (e.g., DNA segments) comprised within the one or more sample fluids 108. Potential hybridization reactions between the one or more molecular probes and/or the one or more genetic code sequences (e.g., DNA segments) can be facilitated using enzymatic hybridization techniques and/or temperature based hybridization techniques. For example, the one or more sample fluids 108 can be annealed to a temperature ranging from, but not limited to, greater than or equal to 50 degrees Celsius ("° C.") and less than or equal to 100° C. (e.g., 95° C.). Wherein the one or more genetic code sequences (e.g., DNA segments) comprise the one or more target nucleic acid sequences, the one or more molecule probes can bond to the target nucleic acid sequences (e.g., as facilitated by the enzymatic hybridization techniques and/or temperature based hybridization techniques). Wherein the one or more genetic code sequences (e.g., DNA segments) do not comprise the one or more target nucleic acid sequences, the one or more molecular probes can remain in the one or more sample fluids 108 without hybridizing with the one or more genetic code sequences (e.g., DNA segments). Moreover, in one or more embodiments, the one or more sample fluids 108 can be prepared off a LOC comprising the microfluidic channel 100 and/or can be loaded onto the LOC, and/or can thereby enter the microfluidic channel 100, subsequent to preparation. Also, in various embodiments the one or more sample fluids 108 can be prepared on a LOC comprising the microfluidic channel 100.

A third flow path 308 that can characterize the flow of the one or more molecular probes. FIG. 3 depicts an exemplary third flow path 308, wherein the one or more molecular probes can be bonded to one or more first genetic code sequences (e.g., first DNA segments) comprised within the one or more sample fluids 108. The one or more first genetic code sequences (e.g., first DNA segments) can comprise the target nucleic acid sequence and/or can be greater than the one or more critical diameters of the one or more nano-DLD arrays 102. Therefore, the one or more molecular probes can bond (e.g., covalently) to the one or more first genetic code sequences (e.g., first DNA segments) and/or thereby be subjected to the same displacement (e.g., lateral displacement in the direction represented by the "LD" arrow) as the one or more first genetic code sequences (e.g., first DNA segments). In contrast, one or more second genetic code sequences (e.g., second DNA segments) comprised within the one or more sample fluids 108 can be characterized as being smaller than the one or more critical diameters and/or not comprising the target nucleic acid sequence. Therefore, the one or more second genetic code sequences (e.g., second DNA segments) can follow the second flow path 116, as depicted in FIGS. 1 and 2, wherein the genetic code sequences (e.g., second DNA segments) can zig-zag through the one or more nano-DLD arrays 102 with minimal lateral displacement.

Thus, in one or more embodiments wherein the one or more one or more first genetic code sequences (e.g., first DNA segments) comprised within the one or more sample fluids 108 can be larger than or equal to the one or more critical diameters and/or can comprise the one or more target nucleic acid sequences, the one or more molecular probes can bond to the one or more first genetic code sequences (e.g., first DNA segments) and thereby be laterally displaced by the one or more nano-DLD arrays 102 (e.g., as exemplified by the third flow path 308). Further, the one or more molecular probes can exit the microfluidic channel 100 via a third concentrated stream (e.g., represented by arrow "C") located in and/or near a collection region (e.g., collection all 114). For example, the third concentrated stream can comprise the one or more first genetic code sequences (e.g., first DNA segments) and/or the one or more bonded molecular probes.

While FIG. 3 depicts a focus injection configuration wherein the one or more sample fluids 108 are provided adjacent to a side wall 110 of the microfluidic channel 100, the various properties and/or features illustrated and/or described herein can be practiced with a focus injection configuration wherein the one or more sample fluids 108 are provided in a different region of the one or more inlets 104 (e.g., a central region as depicted in FIG. 2). Further, while FIG. 3 depicts supplying the one or more sample fluids 108 to the microfluidic channel 100 in accordance with a focus injection configuration, the various properties and/or features illustrated and/or described herein can be practiced in accordance with a full-width injection configuration (e.g., as depicted in FIG. 1).

The one or more sensors 302 can facilitate detection of the one or more molecular probes as the one or more molecular probes traverse the one or more nano-DLD arrays 102 and/or exit the microfluidic channel 100. While FIG. 3 depicts a sensor 302 positioned downstream (e.g., along the flow direction represented by the "F" arrow) of the one or more outlets 106, the architecture of the microfluidic channel 100 is not so limited. For example, the sensor 302 can be positioned between the one or more inlets 104 and/or the one or more outlets 106. Moreover, the sensor 302 can be positioned adjacent to and/or within the one or more inlets 104 and/or outlets 106. Further, the microfluidic channel 100 can comprise a plurality of sensors 302 at respective locations throughout the microfluidic channel 100 (e.g., between the one or more inlets 104 and the one or more outlets 106, downstream of the one or more outlets 106, and/or adjacent to and/or within the one or more inlets 104 and/or outlets 106).

The one or more sensors 302 can facilitate detection of the location of the one or more molecular probes as the one or more molecular probes exit the one or more outlets 106 and/or as the one or more molecular probes traverse the one or more nano-DLD arrays 102. The one or more sensors 302 can comprise, but not limited to: biosensors, electrochemical sensors, photosensors, optical light absorption sensors, a combination thereof, and/or the like. The one or more sensors 302 can detect: a position of the one or more molecular probes within the one or more nano-DLD arrays 102, a region of the one or more outlets 106 from which the one or more molecular probes have exited, individual single molecule counts of respective molecular probes and/or molecules comprising the target nucleic acid sequences, a combination thereof, and/or the like.

The one or more sensors 302 can be operably coupled to one or more controllers 304 via one or more networks 306. The one or more networks 306 can comprise wired and wireless networks, including, but not limited to, a cellular network, a wide area network (WAN) (e.g., the Internet) or a local area network (LAN). For example, the one or more sensors 302 can communicate with the one or more controllers 304 (and vice versa) using virtually any desired wired or wireless technology including for example, but not limited to: cellular, WAN, wireless fidelity (Wi-Fi), Wi-Max, WLAN, BLUETOOTH® technology, a combination thereof, and/or the like. Additionally, the one or more networks 306 can comprise and/or be located within a cloud computing environment.

The one or more controllers 304 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. A user of the system 300 (e.g., via use of a LOC comprising the microfluidic channel 100) can utilize the one or more controllers 304 to view and/or analyze one or more detections made by the one or more sensors 302. For example, the one or more sensors 302 can send data (e.g., regarding detections) to the one or more controllers 304 (e.g., via a direct connection and/or via the one or more networks 306). In one or more embodiments, the one or more controllers 304 can determine, based on the detections of the one or more sensors 302, the third flow path 308 traversed by the one or more molecules (e.g., molecular probes) through the one or more nano-DLD arrays 102. For example, the one or more controllers 304 can determine whether the third flow path 308 exhibits lateral displacement towards a collection region and/or whether the third flow path 308 exhibits a zig-zag path through the one or more nano-DLD arrays 102 with minimal lateral displacement. Moreover, based on the determined flow path, the one or more controllers 304 can determine whether the one or more sample fluids 108 comprise the one or more target nucleic acid sequences. Furthermore, based on said determinations, the one or more controllers 304 can determine: whether the one or more sample fluids 108 are subject to a given health condition and/or trait, and/or a likelihood (e.g., a percentage) that the one or more sample fluids 108 are subject to a given health condition and/or trait. For example, wherein a given health condition and/or trait can be characterized by a plurality of defined nucleic acid sequences, the one or more controllers 304 can determine a likelihood that the one or more sample fluids 108 are subjected to the given health condition and/or trait based on the number of defined nucleic acid sequences determined to be present in the one or more sample fluids 108.

Additionally, the one or more controllers 304 can comprise one or more displays that can present one or more outputs detected by the one or more sensors 302 and/or determined by the one or more controllers 304 (e.g., by one or more processors comprised within the one or more controllers 304) to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

Figure 4:
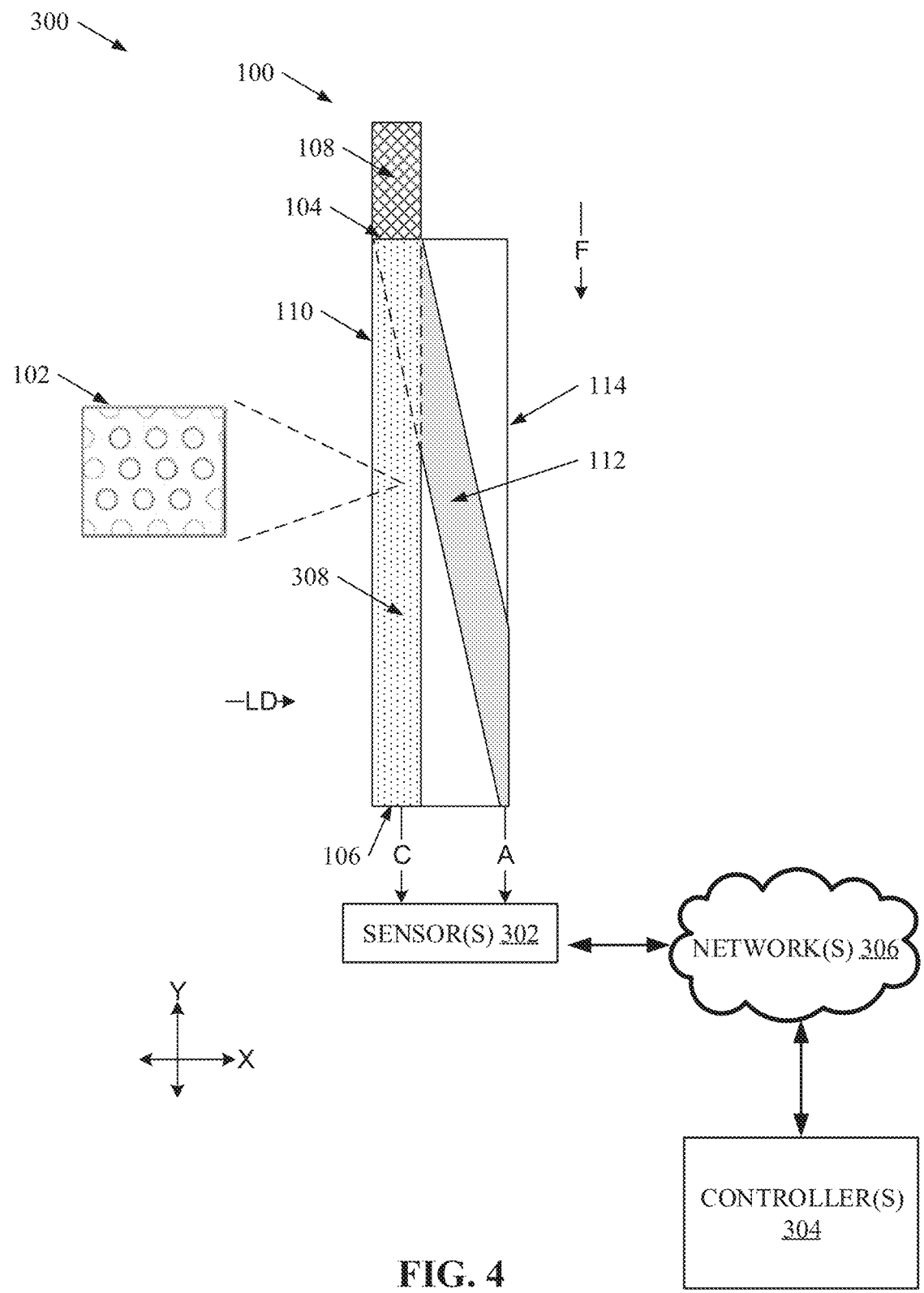
FIG. 4 illustrates a diagram of an example, non-limiting system that can comprise a microfluidic channel and can comprise facilitate detecting one or more defined nucleic acid sequences in accordance with one or more embodiments described herein.

FIG. 4 illustrates a diagram of the example, non-limiting microfluidic channel 100 that can facilitate detection of one or more molecular probes comprised within the one or more sample fluids 108 in accordance with one or more embodiments described herein. Repetitive description of like elements employed in other embodiments described herein is omitted for sake of brevity.

FIG. 4 depicts an exemplary third flow path 308, wherein the one or more molecular probes can travel through the one or more nano-DLD arrays 102 without being bonded to the one or more genetic code sequences (e.g., DNA segments). For example, the one or more genetic code sequences (e.g., DNA segments) comprised within the one or more sample fluids 108 can comprise nucleic acid sequences other than the one or more target nucleic acid sequences. Wherein the one or more genetic code sequences (e.g., DNA segments) are larger than the one or more critical diameters of the one or more nano-DLD arrays 102, the one or more genetic code sequences (e.g., DNA segments) can follow the first flow path 112 in which the one or more genetic code sequences (e.g., DNA segments) are subject to lateral displacement towards a collection region (e.g., as depicted in FIGS. 1-2). In contrast, wherein the one or more molecular probes are smaller than the one or more critical diameters of the one or more nano-DLD arrays 102, the third flow path 308 of the one or more molecular probes can zig-zag through the one or more nano-DLD arrays 102 with minimal lateral displacement.

The non-bonded molecular probes can thereby zig-zag through the one or more nano-DLD arrays 102 in a stream (e.g., represented by the "C" arrow) separate and/or distinct from a concentrated stream (e.g., represented by the "A" arrow) of the one or more bumped genetic code sequences (e.g., DNA sequences). In one or more embodiments, the one or more sample fluids 108 can comprise the one or more molecular probes and only genetic code sequences (e.g., DNA segments) that are larger than the one or more critical diameters of the one or more nano-DLD arrays 102. Thus, the zig-zag stream (e.g., represented by the "C" arrow) can comprise the one or more non-bonded molecular probes without the one or more genetic code sequences (e.g., DNA segments). Also, in one or more embodiments, the one or more sample fluids 108 can comprise the one or more molecular probes and/or a plurality of genetic code sequences (e.g., DNA segments) with respective sizes greater than or equal to the one or more critical diameters of the one or more nano-DLD arrays 102 and/or respective sizes less than the one or more critical diameters of the one or more nano-DLD arrays 102. Thus, the zig-zag stream (e.g., represented by the "C" arrow) can comprise both the one or more non-bonded molecular probes and/or one or more respective genetic code sequences (e.g., DNA segments) that are smaller than the one or more critical diameters of the one or more nano-DLD arrays 102.

While FIG. 4 depicts a focus injection configuration wherein the one or more sample fluids 108 are provided adjacent to a side wall 110 of the microfluidic channel 100, the various properties and/or features illustrated and/or described herein can be practiced with a focus injection configuration wherein the one or more sample fluids 108 are provided in a different region of the one or more inlets 104 (e.g., a central region as depicted in FIG. 2). Further, while FIG. 3 depicts supplying the one or more sample fluids 108 to the microfluidic channel 100 in accordance with a focus injection configuration, the various properties and/or features illustrated and/or described herein can be practiced in accordance with a full-width injection configuration (e.g., as depicted in FIG. 1).

Figure 5:
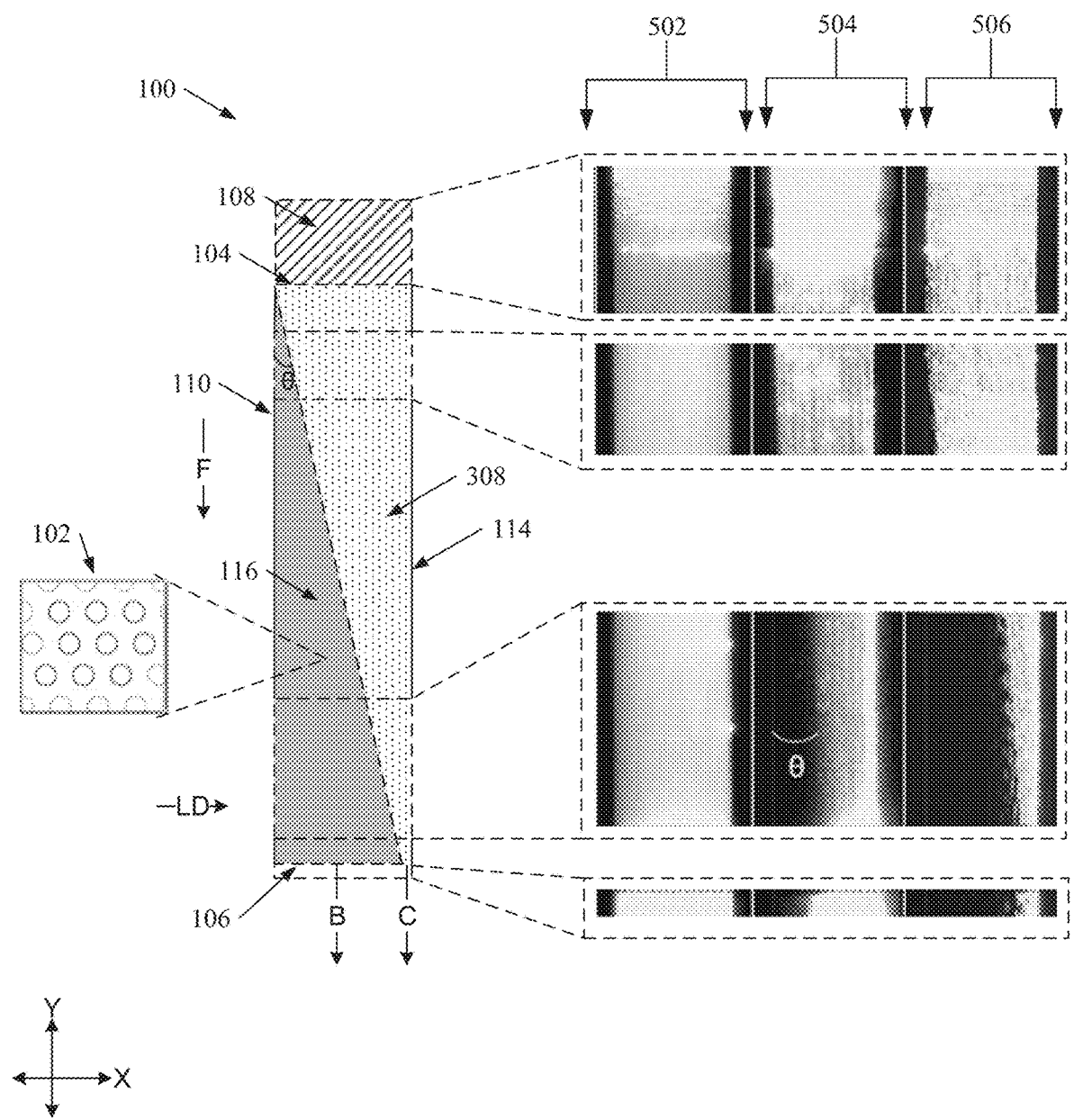
FIG. 5 illustrates a plurality of example, non-limiting photos of one or more fluid samples traversing through a microfluidic channel that can comprise one or more deterministic lateral displacement arrays, which can separate deoxyribonucleic acid sequences based on size in accordance with one or more embodiments described herein.

FIG. 5 illustrates a diagram of the example, non-limiting microfluidic channel 100 with perspectives of the microfluidic channel 100 exemplified by a plurality of photos in accordance with one or more embodiments described herein. Repetitive description of like elements employed in other embodiments described herein is omitted for sake of brevity. As shown if FIG. 5, the sample fluid 108 can comprise one or more genetic code sequences (e.g., DNA segments) and/or molecular probes traversing a microfluidic channel 100 that can be characterized by a full-width injection configuration.

In one or more embodiments, a first column 502 of photos presented in FIG. 5 can illustrate the second flow path 116 of one or more genetic code sequences (e.g., DNA segments) that are smaller than the one or more critical diameters of the one or more nano-DLD arrays 102. Additionally, in one or more embodiments, the first column 502 of photos presented in FIG. 5 can illustrate the third flow path 308 of the one or more molecular probes, wherein the one or more genetic code sequences (e.g., DNA segments) do not comprise the one or more target nucleic acid sequences (e.g., the one or more genetic code sequences comprise nucleic acid sequences other than the one or more target nucleic acid sequences). Thus, the first column 502 can depict one or more molecules (e.g., one or more genetic code sequences smaller than the one or more critical diameters of the one or more nano-DLD arrays 102 and/or one or more non-bonded molecular probes) following a zig-zag path through the one or more nano-DLD arrays 102 with minimal lateral displacement.

In one or more embodiments, a second column 504 of photos presented in FIG. 5 can illustrate the first flow path 112 of one or more genetic code sequences (e.g., DNA segments) that can be larger than the one or more critical diameters of the one or more nano-DLD arrays 102. Additionally, in one or more embodiments, the second column 504 of photos presented in FIG. 5 can illustrate the third flow path 308 of the one or more molecular probes wherein the one or more genetic code sequences (e.g., DNA segments) can comprise the one or more target nucleic acid sequences, thereby facilitating bonding between the one or more genetic code sequences and/or the one or more molecular probes. Thus, the second column 504 can depict one or more molecules (e.g., one or more genetic code sequences larger than the one or more critical diameters of the one or more nano-DLD arrays 102 and/or one or more bonded molecular probes) partially bumped towards a collection region (e.g., collection wall 114) while traversing through the one or more nano-DLD arrays 102.

In one or more embodiments, a third column 506 of photos presented in FIG. 5 can illustrate the first flow path 112 of one or more genetic code sequences (e.g., DNA segments) that can be larger than the one or more critical diameters of the one or more nano-DLD arrays 102. Wherein the subject one or more genetic code sequences (e.g., DNA segments) can exhibit greater lateral displacement than the partially bumped molecules depicted in the second column 504. Additionally, in one or more embodiments, the second column 504 of photos presented in FIG. 5 can illustrate the third flow path 308 of the one or more molecular probes wherein the one or more genetic code sequences (e.g., DNA segments) can comprise the one or more target nucleic acid sequences, thereby facilitating bonding between the one or more genetic code sequences and/or the one or more molecular probes. Wherein the subject one or more bonded molecular probes can exhibit greater lateral displacement than the partially bumped molecules depicted in the second column 504. Thus, the third column 506 can depict one or more molecules (e.g., one or more genetic code sequences larger than the one or more critical diameters of the one or more nano-DLD arrays 102 and/or one or more bonded molecular probes) fully bumped towards a collection region (e.g., collection wall 114) while traversing through the one or more nano-DLD arrays 102.

Figure 6:
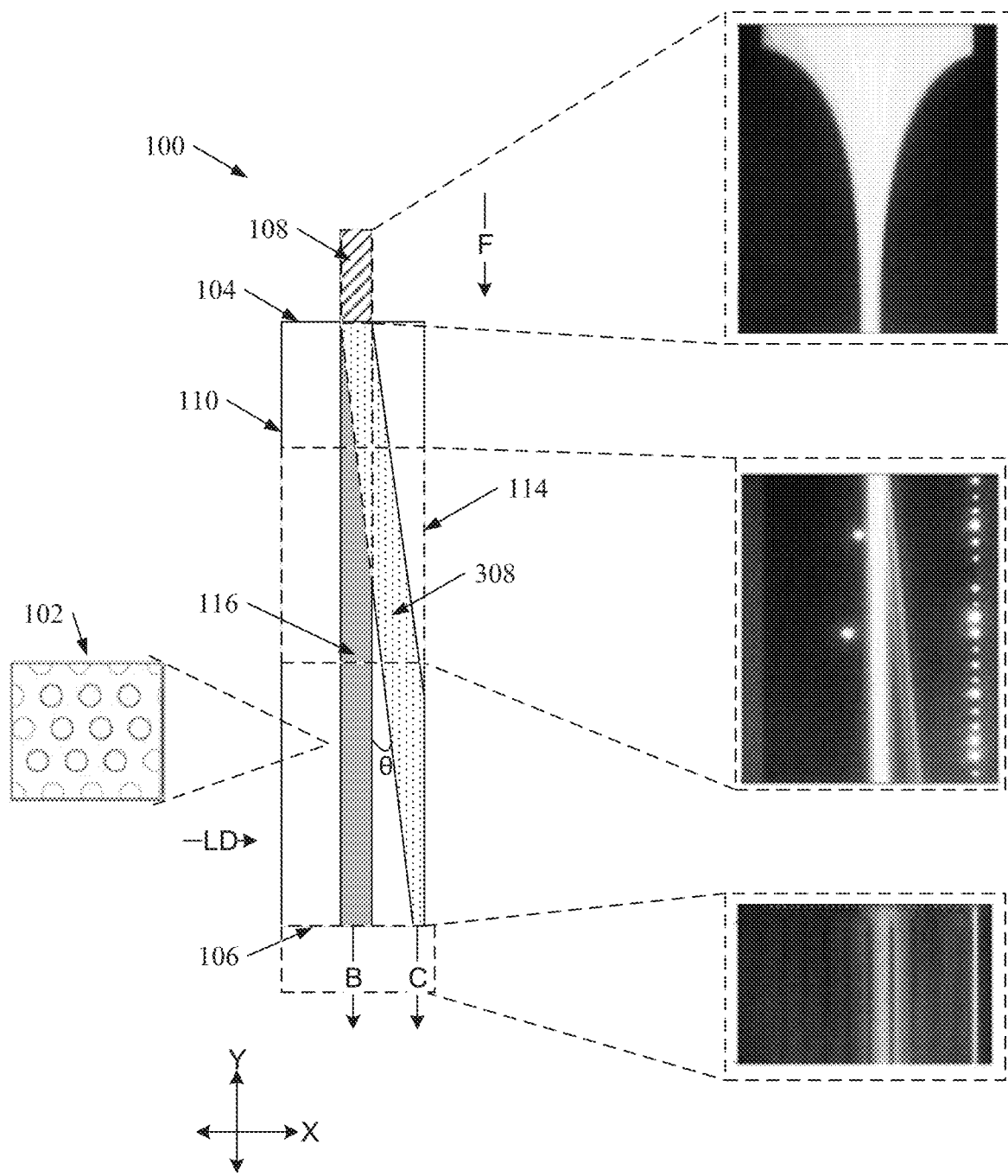
FIG. 6 illustrates a plurality of example, non-limiting photos of one or more fluid samples traversing through a microfluidic channel that can comprise one or more deterministic lateral displacement arrays, which can separate deoxyribonucleic acid sequences based on size in accordance with one or more embodiments described herein.

FIG. 6 illustrates a diagram of the example, non-limiting microfluidic channel 100 with perspectives of the microfluidic channel 100 exemplified by a plurality of photos in accordance with one or more embodiments described herein. Repetitive description of like elements employed in other embodiments described herein is omitted for sake of brevity. As shown if FIG. 6, the sample fluid 108 can comprise one or more genetic code sequences (e.g., DNA segments) and/or molecular probes traversing a microfluidic channel 100 that can be characterized by a focus injection configuration.

FIG. 6 presents three photos that can exemplify the fluid behavior of the one or more sample fluids 108 during entry into the one or more nano-DLD arrays 102, travel through the one or more nano-DLD arrays 102, and/or exit from the one or more nano-DLD arrays 102. A first photo 602 can depict the one or more sample fluids 108 being focused to a particular region of the one or more inlets 104 (e.g., a central region). A second photo 604 can depict separation of one or more first genetic code sequences (e.g., DNA segments) and/or molecular probes from one or more second genetic code sequences (e.g., small DNA sequences following the second flow path 116, which can be a zig-zag path). The one or more first genetic code sequences can be covalently bonded to one or more molecular probes and can be bumped (e.g., laterally displaced) towards a collection region (e.g., as characterized by third flow path 308 in FIG. 6). A third photo 606 can depict two distinct streams exiting the one or more outlets 106. A first stream (e.g., represented by the "B" arrow) can comprise the one or more second genetic code sequences (e.g., DNA segments smaller than the one or more critical diameters of the one or more nano-DLD arrays 102). A second stream (e.g., represented by the "C" arrow) can comprise the one or more molecule probes bonded to the one or more first genetic code sequences (e.g., DNA segments smaller than the one or more critical diameters of the one or more nano-DLD arrays 102).

Figure 7:
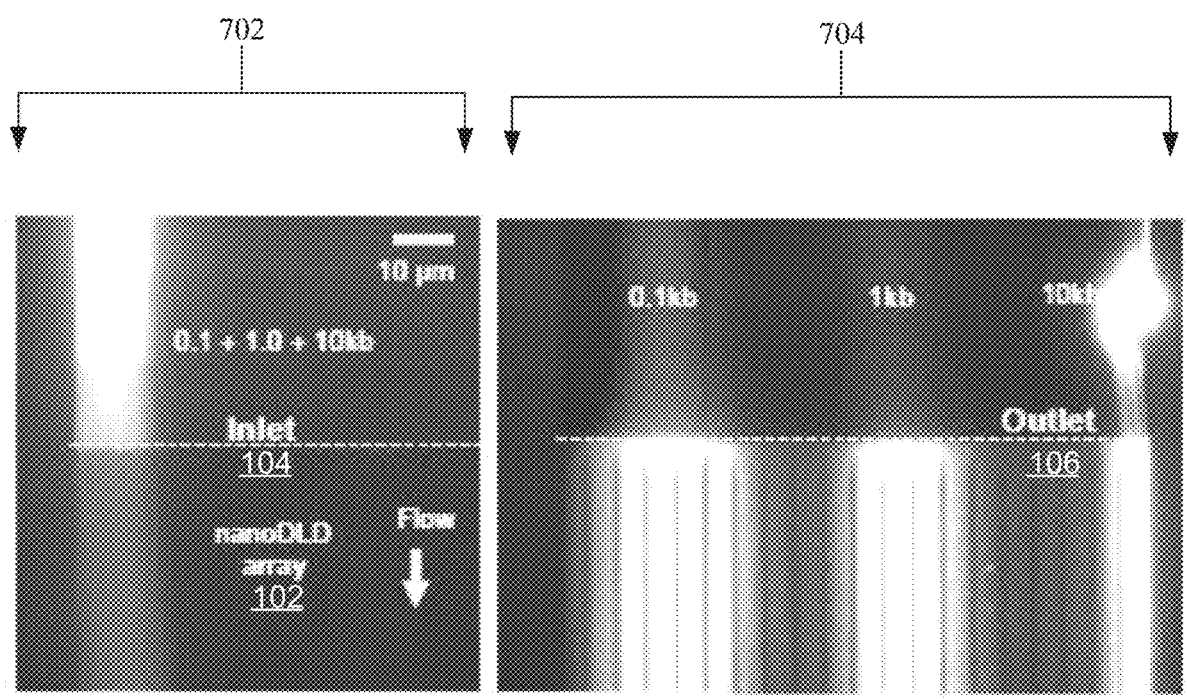
FIG. 7 illustrates a plurality of example, non-limiting photos of one or more fluid samples as the samples enter and/or exit a microfluidic channel that can comprise one or more deterministic lateral displacement arrays, which can separate deoxyribonucleic acid sequences based on size in accordance with one or more embodiments described herein.

FIG. 7 illustrates a photo of the example, non-limiting microfluidic channel 100 in accordance with one or more embodiments described herein. Repetitive description of like elements employed in other embodiments described herein is omitted for sake of brevity. The microfluidic channel 100 depicted in FIG. 7 can be characterized as having a focus injection configuration. FIG. 7 illustrates that in various embodiments the microfluidic channel 100 can facilitate separation of genetic code sequences based on two or more size thresholds.

A left portion 702 of the photo presented in FIG. 7 can regard an end of the microfluidic channel 100 comprising the one or more inlets 104. Further, a right portion 704 of the photo presented in FIG. 7 can regard an opposite end of the microfluidic channel 100 comprising the one or more outlets 106. The highlighted streams shown in FIG. 7 can represent genetic code sequences (e.g., DNA segments). As shown in FIG. 7, one or more sample fluids 108, which can comprise one or more first genetic code sequences (e.g., 0.1 kilobases (kb) in size), one or more second genetic code sequences (e.g., 1.0 kb in size), and/or one or more third genetic code sequences (e.g., 10 kb in size), can enter the one or more nano-DLD arrays 102. As the one or more sample fluids 108 flow through the microfluidic channel 100, the one or more nano-DLD arrays 102 can separate the genetic code sequences comprising the one or more sample fluids 108 based on size. Thus, the one or more nano-DLD arrays 102 can form three streams of genetic code sequences. A first stream can comprise the one or more first genetic code sequences. A second stream can comprise the one or more second genetic code sequences. Also, a third stream can comprise the one or more third genetic code sequences.

Thus, various embodiments described herein can regard a microfluidic channel 100 that can be positioned on a LOC device and can separate genetic code sequences (e.g., DNA segments) of one or more sample fluids 108 based on size (e.g., from other genetic code sequences and/or other molecules). For example, the microfluidic channel 100 can utilize one or more nano-DLD arrays 102 in conjunction with full-width injection and/or focus injection configurations to facilitate the size-based separation. Further, one or more molecular probes (e.g., labelled with fluorescent, electromagnetic, and/or electrochemical tags) can be introduced to the one or more sample fluids 108, wherein the one or more molecular probes can have an affinity to bond (e.g., covalently) to a defined nucleic acid sequence. Large genetic code sequences (e.g., DNA segments) that are greater than the one or more critical diameters of the one or more nano-DLD arrays 102 can be laterally displaced (e.g., bumped) towards a collection region (e.g., a collection wall 1114) to form a concentrated stream (e.g., streams represented by arrows "A" and/or "C"). Molecules smaller than the one or more critical diameters of the one or more nano-DLD arrays 102, such as the one or more molecular probes and/or small genetic code sequences comprised within the one or more sample fluids 108, can zig-zag through the one or more nano-DLD arrays 102 with minimal lateral displacement.

In one or more embodiments, wherein the one or more genetic code sequences (e.g., DNA segments) comprise the one or more defined nucleic acid sequence, a hybridization can occur between the one or more genetic code sequences and the one or more molecular probes (e.g., facilitated by enzymatic and/or annealing techniques). For example, the one or more large genetic code sequences can comprise the one or more target nucleic acid sequences. In another example, the one or more small genetic code sequences can comprise the one or more target nucleic acid sequences, wherein the hybridization results in a product that is larger than the one or more critical diameters of the one or more nano-DLD arrays 102. By bonding to the one or more genetic sequences, the one or more molecular probes can experience lateral displacement and travel along a bumped path rather than the zig-zag path the one or more molecular probes would otherwise experience. One or more sensors 302 can detect the location and/or flow path of the one or more molecular probes at one or more positions throughout the microfluidic channel 100 and can communicate with one or more controllers 304 (e.g., via one or more networks 306). The one or more controllers 304 can comprise computerized equipment to facilitate determining whether the one or more molecular probes have experiences a bumped path and/or a zig-zag path through the microfluidic channel 100.

Wherein the one or more controllers 304 determine that the one or more molecular probes have experienced a zig-zag path through the microfluidic channel 100, the one or more controllers 304 can further conclude that the one or more sample fluids 108 do not comprise the target nucleic acid sequence. In contrast, wherein the one or more controllers 304 determine that the one or more molecular probes have experienced a bumped path through the microfluidic channel 100, the one or more controllers 304 can further conclude that the one or more sample fluids 108 do comprise the one or more target nucleic acid sequence. The one or more target nucleic acid sequence can be indicative of one or more health conditions and/or traits, such as, but not limited to: a disease, a virus, a bacterium, a mutation, fetal development, physical traits, a combination thereof, and/or the like. Thus, whether or not the one or more sample fluids 108 comprises the one or more target nucleic acid sequence can be indicative of whether or not a source of the one or more sample fluids 108 is subject to a given disease, virus, bacteria, health condition, mutation, combination thereof, and/or the like.

For example, the presence of a target nucleic acid sequence can be indicative of the presence of a particular disease. The one or more controllers 304 can determine whether the disease exists in the one or more sample fluids 108 based on the one or more detections of the one or more sensors 302. In another example, a health condition and/or trait can be characterized by a plurality of respective target nucleic acid sequences (e.g., target nucleic acid sequences characterized by different sequences). The one or more sample fluids 108 can comprise a plurality of molecular probes with respective affinities to bond to the respective target nucleic acid sequences and can be tagged with respective label identifiers. Thus, the positioning and/or travel of respective molecular probes can be detected by the one or more sensors 302. Therefore, the one or more controllers 304 can determine how many, if any, of the plurality of respective target nucleic acid sequences can be present in the one or more sample fluids 108. Based on said determination, the one or more controllers 304 can compute a likelihood (e.g., a percentage) that the source of the one or more sample fluids 108 is subject to the given health condition and/or trait.

In another example, the one or more sample fluids 108 can be derived from a food source. A plurality of molecular probes can be introduced to the one or more sample fluids 108, wherein respective molecular probes can have respective affinities to bond to respective nucleic acid sequences and/or respective labels (e.g., tagged with respective fluorescence markers). The one or more sample fluids 108 can be subjected to conditions that can facilitate hybridization of the one or more molecular probes (e.g., annealing of the one or more sample fluids 108). Additionally, the one or more sample fluids 108 can be introduced into the microfluidic channel 100. The one or more sensors 302 can detect the position and/or flow path of the respective molecular probes. Based on said detections, the one or more controllers 304 can determine which, if any, respective target nucleic acid sequences are comprised within the one or more sample fluids 108. Based on said determinations, the one or more controllers 304 can further determine whether the subject food source is compliant with one or more defined conditions regarding the respective nucleic acid sequences. Additionally, the one or more controllers 304 can present the determinations to a user of the system 300.

Figure 8:
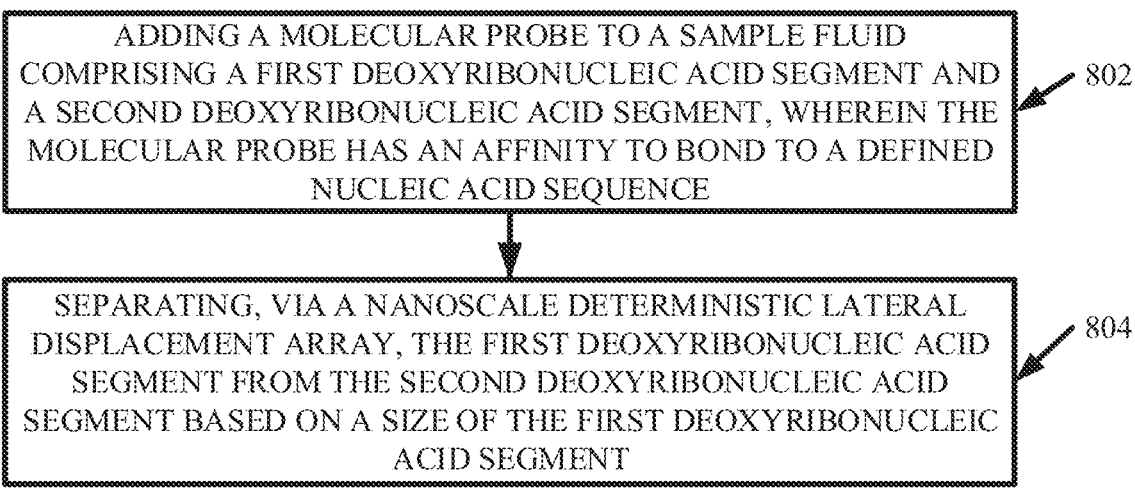
FIG. 8 illustrates a flow diagram of an example, non-limiting method that can facilitate detecting whether one or more target deoxyribonucleic acid sequences are present in a fluid sample in accordance with one or more embodiments described herein.

FIG. 8 illustrates a flow diagram of an example, non-limiting method 800 that can facilitate detection of one or more defined nucleic acid sequences utilizing the microfluidic channel 100 and/or system 300 in accordance with one or more embodiments described herein. Repetitive description of like elements employed in other embodiments described herein is omitted for sake of brevity.

At 802, the method 800 can comprise adding one or more molecular probes to one or more sample fluids 108 comprising one or more first DNA segments and/or one or more second DNA segments, wherein the molecular probe can have an affinity to bond to a defined nucleic acid sequence. The adding at 802 can be performed, for example, on a LOC device via one or more microfluid devices such as a micropump (e.g., integrated on the LOC and/or external to the LOC). The one or more molecular probes can comprise a nucleic acid sequence that is complimentary to the defined nucleic acid sequence to facilitate the bonding affinity.

At 804, the method 800 can comprise separating, via one or more nano-DLD arrays 102, the one or more first DNA segments from the one or more second DNA segments based on a size of the one or more first DNA segments. For example, the one or more first DNA segments can be larger than the one or more critical diameters of the one or more nano-DLD arrays 102 and thereby be bumped towards one or more collection regions (e.g., a collection wall 114). Wherein the one or more first DNA segments comprise the defined nucleic acid sequence, the one or more molecular probes can bond to the one or more first DNA segments and can thereby be bumped towards the one or more collection regions. Wherein the one or more first DNA segments do not comprise the defined nucleic acid sequence, the one or more molecular probes can zig-zag through the one or more nano-DLD arrays 102 with minimal lateral displacement.

Further, one or more sensors 302 can detect the position and/or flow path of the one or more molecular probes (e.g., via one or more fluorescent, electromagnetic, and/or electrochemical tags on the molecular probes). Moreover, based on said detection, one or more controllers 304 can determine whether the one or more sample fluids 108 comprise the target nucleic acid sequence.

FIG. 9 illustrates a flow diagram of an example, non-limiting method 900 that can also facilitate detection of one or more defined nucleic acid sequences utilizing the microfluidic channel 100 and/or system 300 in accordance with one or more embodiments described herein. Repetitive description of like elements employed in other embodiments described herein is omitted for sake of brevity.

At 902, the method 900 can comprise adding one or more molecular probes to one or more sample fluids 108 comprising one or more first DNA segments and/or one or more second DNA segments, wherein the molecular probe can have an affinity to bond to a defined nucleic acid sequence. The adding at 802 can be performed, for example, on a LOC device via one or more microfluid devices such as a micropump (e.g., integrated on the LOC and/or external to the LOC). The one or more molecular probes can comprise a nucleic acid sequence that is complimentary to the defined nucleic acid sequence to facilitate the bonding affinity.

At 904, the method 900 can comprise annealing the one or more molecular probes and/or the one or more sample fluids 108 to facilitate a chemical reaction (e.g., hybridization) between the one or more molecular probes and the one or more sample fluids 108 (e.g., the one or more first DNA segments and/or the one or more second DNA segments). For example, the one or more molecular probes and/or the one or more sample fluids 108 can be heated to a temperature ranging from, but not limited to 50 degrees Celsius ("° C.") and less than or equal to 100° C. (e.g., 95° C.). Wherein the one or more first DNA segments comprise the defined nucleic acid sequence, the one or more molecular probes can bond to the one or more first DNA segments as a result of the annealing. Wherein the one or more first DNA segments do not comprise the defined nucleic acid sequence, the one or more molecular probes can remain non-bonded to the one or more genetic code sequences comprising the one or more sample fluids 108.

At 906, the method 900 can comprise separating, via one or more nano-DLD arrays 102, the one or more first DNA segments from the one or more second DNA segments based on a size of the one or more first DNA segments. For example, the one or more first DNA segments can be larger than the one or more critical diameters of the one or more nano-DLD arrays 102 and thereby be bumped towards one or more collection regions (e.g., a collection wall 114). In contrast, the one or more second DNA segments and/or one or more non-bonded molecular probes can be smaller than the one or more critical diameters of the one or more nano-DLD arrays 102 and thereby zig-zag through the one or more nano-DLD arrays 102 with minimal lateral displacement.

At 908, the method 900 can comprise detecting, by one or more sensors 302, a location of the one or more molecular probes. The one or more molecular probes can be labelled using fluorescence, electromagnetic, and/or electrochemical labelling techniques. The detecting at 908 can comprise optical detection and/or electrical detection. Further, the one or more sensors 302 can send data regarding the one or more detections to one or more controllers 304 (e.g., via one or more networks 306).

At 910, the method 900 can comprise determining, by a system 300 operatively coupled to one or more processors (e.g., comprised within the one or more controllers 304), a flow path of the one or more molecular probes through the one or more nano-DLD arrays 102 based on the location detected at 908. For example, the one or more controllers 304 can determine whether the one or more molecular probes experienced a bumped flow path (e.g., lateral displacement towards a collection region) or a zig-zag flow path (e.g., travel with minimal lateral displacement) through the one or more nano-DLD arrays 102.

At 912, the method 900 can also comprise determining, by the system 300, whether the one or more sample fluids 108 comprise the defined nucleic acid sequence based on the flow path determined at 910. For example, determining that the one or more molecular probes experienced a bumped flow path can be indicative that the one or more sample fluids 108 comprise the defined nucleic acid sequence.

FIG. 10 illustrates a flow diagram of an example, non-limiting method 1000 that can also facilitate detection of one or more defined nucleic acid sequences utilizing the microfluidic channel 100 and/or system 300 in accordance with one or more embodiments described herein. Repetitive description of like elements employed in other embodiments described herein is omitted for sake of brevity.

At 1002, the method 1000 can comprise annealing one or more sample fluids 108 comprising one or more probe molecules (e.g., molecular probes), one or more first DNA segments, and/or one or more second DNA segments. The one or more probe molecules (e.g., molecular probes) can bond to the one or more first DNA segments based on the one or more first DNA segments comprising a defined nucleic acid sequence. For example, the one or more molecular probes and/or the one or more sample fluids 108 can be heated to a temperature ranging from, but not limited to 50 degrees Celsius ("° C.") and less than or equal to 100° C. (e.g., 95° C.). The one or more probe molecules (e.g., molecular probes) can be labelled using fluorescence, electromagnetic, and/or electrochemical labelling techniques.

At 1004, the method 1000 can comprise separating, via one or more nano-DLD arrays 102, the one or more first DNA segments from the one or more second DNA segments based on a size of the one or more first DNA segments. For example, the one or more first DNA segments can be larger than one or more critical diameters of the one or more nano-DLD arrays 102 and thereby be bumped (e.g., laterally displaced) towards one or more collection regions (e.g., a collection wall 114 and/or a collection channel).

Further, one or more sensors 302 can detect the position and/or flow path of the one or more probe molecules (e.g., via one or more fluorescent, electromagnetic, and/or electrochemical tags on the molecular probes). Moreover, based on said detection, one or more controllers 304 can determine whether the one or more sample fluids 108 comprise the target nucleic acid sequence.

FIG. 11 illustrates a flow diagram of an example, non-limiting method 1100 that can also facilitate detection of one or more defined nucleic acid sequences utilizing the microfluidic channel 100 and/or system 300 in accordance with one or more embodiments described herein. Repetitive description of like elements employed in other embodiments described herein is omitted for sake of brevity.

At 1102, the method 1100 can comprise adding one or more molecular probes to one or more sample fluids 108 comprising a DNA segment, wherein the molecular probe can have an affinity to bond to a defined nucleic acid sequence. The one or more molecular probes can be labelled using fluorescence, electromagnetic, and/or electrochemical labelling techniques. Further, the one or more molecular probes and/or the one or more sample fluids 108 can be under annealing to facilitate potential hybridization reactions.

At 1104, the method 1100 can comprise displacing, via one or more nano-DLD arrays 102 comprised within a microfluidic channel 100, the DNA segment towards and/or into a collection region (e.g., a collection wall 114 and/or a collection channel) of the microfluidic channel 100. The one or more nano-DLD arrays 102 can displace one or more molecules having a size greater than a defined threshold (e.g., critical diameter). Further, the size of the one or more molecular probes can be less than the defined threshold. Thus, the one or more nano-DLD arrays 102 can not displace the one or more molecular probes towards and/or into the one or more collection regions unless the one or more molecular probes bond with the one or more DNA segments, thereby increasing in size. Further, the one or more molecular probes can bond with the one or DNA segments wherein the one or more DNA segments comprise the defined nucleic acid sequence.

Further, one or more sensors 302 can detect the position and/or flow path of the one or more molecular probes (e.g., via optical and/or electrical detection). Moreover, based on said detection, one or more controllers 304 can determine whether the one or more sample fluids 108 comprise the defined nucleic acid sequence.

Figure 12:
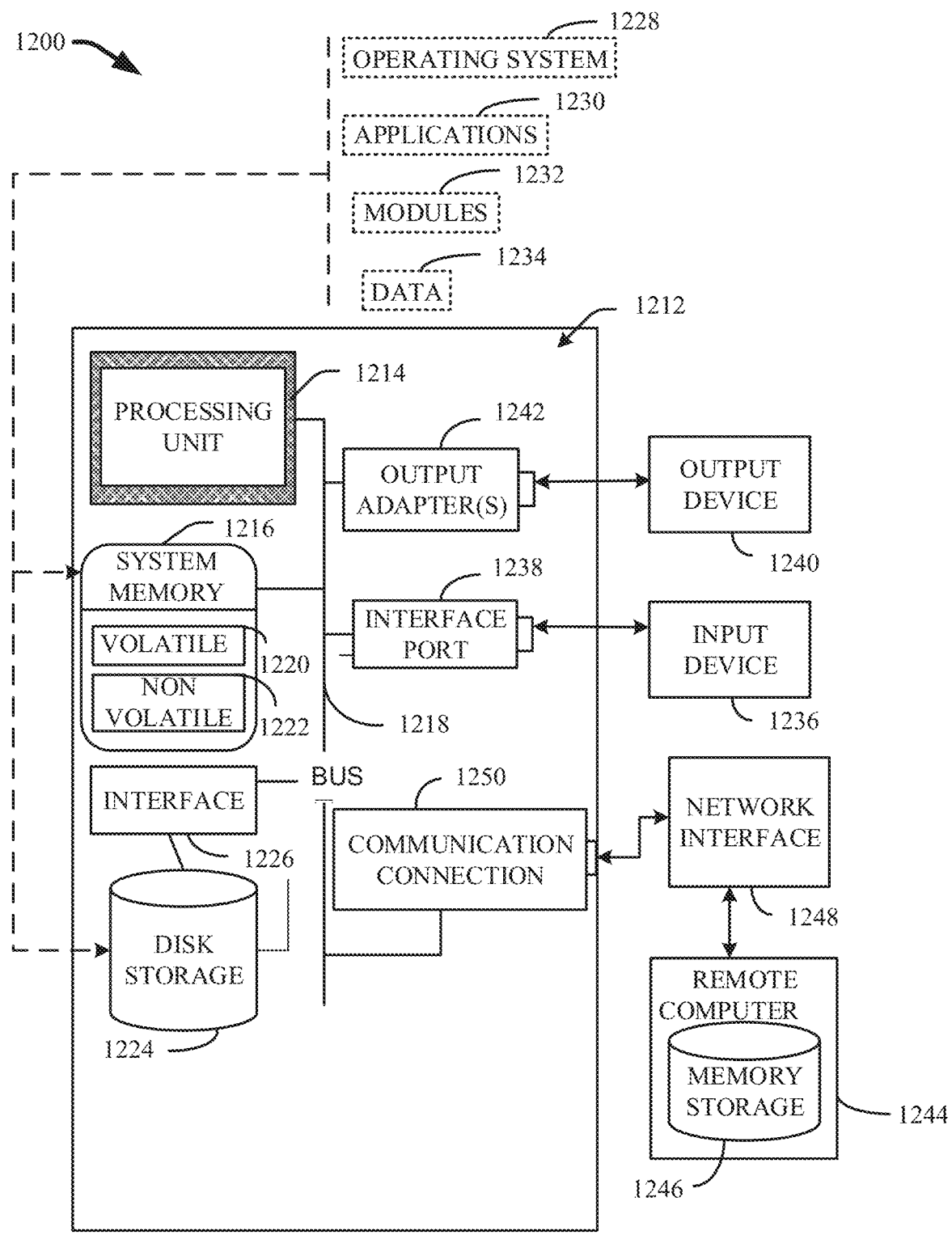
FIG. 12 illustrates a block diagram of an example, non-limiting operating environment in which one or more embodiments described herein can be facilitated.

In order to provide a context for the various aspects of the disclosed subject matter, FIG. 12 as well as the following discussion are intended to provide a general description of a suitable environment in which the various aspects of the disclosed subject matter can be implemented. FIG. 12 illustrates a block diagram of an example, non-limiting operating environment 1200 in which one or more embodiments described herein can be facilitated. For example, the operating environment 1200 can comprise and/or otherwise facilitate one or more features of the one or more controllers 304 described herein in accordance with one or more embodiments. Repetitive description of like elements employed in other embodiments described herein is omitted for sake of brevity. With reference to FIG. 12, a suitable operating environment 1200 for implementing various aspects of this disclosure can include a computer 1212. The computer 1212 can also include a processing unit 1214, a system memory 1216, and a system bus 1218. The system bus 1218 can operably couple system components including, but not limited to, the system memory 1216 to the processing unit 1214. The processing unit 1214 can be any of various available processors. Dual microprocessors and other multiprocessor architectures also can be employed as the processing unit 1214. The system bus 1218 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1216 can also include volatile memory 1220 and nonvolatile memory 1222. The basic input/output system (BIOS), containing the basic routines to transfer information between elements within the computer 1212, such as during start-up, can be stored in nonvolatile memory 1222. By way of illustration, and not limitation, nonvolatile memory 1222 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1220 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1212 can also include removable/non-removable, volatile/non-volatile computer storage media. FIG. 12 illustrates, for example, a disk storage 1224. Disk storage 1224 can also include, but is not limited to, devices like a magnetic disk drive, floppy disk drive, tape drive, Jaz drive, Zip drive, LS-100 drive, flash memory card, or memory stick. The disk storage 1224 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1224 to the system bus 1218, a removable or non-removable interface can be used, such as interface 1226. FIG. 12 also depicts software that can act as an intermediary between users and the basic computer resources described in the suitable operating environment 1200. Such software can also include, for example, an operating system 1228. Operating system 1228, which can be stored on disk storage 1224, acts to control and allocate resources of the computer 1212. System applications 1230 can take advantage of the management of resources by operating system 1228 through program modules 1232 and program data 1234, e.g., stored either in system memory 1216 or on disk storage 1224. It is to be appreciated that this disclosure can be implemented with various operating systems or combinations of operating systems. A user enters commands or information into the computer 1212 through one or more input devices 1236. Input devices 1236 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1214 through the system bus 1218 via one or more interface ports 1238. The one or more Interface ports 1238 can include, for example, a serial port, a parallel port, a game port, and a universal serial bus (USB). One or more output devices 1240 can use some of the same type of ports as input device 1236. Thus, for example, a USB port can be used to provide input to computer 1212, and to output information from computer 1212 to an output device 1240. Output adapter 1242 can be provided to illustrate that there are some output devices 1240 like monitors, speakers, and printers, among other output devices 1240, which require special adapters. The output adapters 1242 can include, by way of illustration and not limitation, video and sound cards that provide a means of connection between the output device 1240 and the system bus 1218. It should be noted that other devices and/or systems of devices provide both input and output capabilities such as one or more remote computers 1244.

Computer 1212 can operate in a networked environment using logical connections to one or more remote computers, such as remote computer 1244. The remote computer 1244 can be a computer, a server, a router, a network PC, a workstation, a microprocessor based appliance, a peer device or other common network node and the like, and typically can also include many or all of the elements described relative to computer 1212. For purposes of brevity, only a memory storage device 1246 is illustrated with remote computer 1244. Remote computer 1244 can be logically connected to computer 1212 through a network interface 1248 and then physically connected via communication connection 1250. Further, operation can be distributed across multiple (local and remote) systems. Network interface 1248 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1250 refers to the hardware/software employed to connect the network interface 1248 to the system bus 1218. While communication connection 1250 is shown for illustrative clarity inside computer 1212, it can also be external to computer 1212. The hardware/software for connection to the network interface 1248 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   forming a sample fluid by adding a molecular probe to a fluid comprising a first deoxyribonucleic acid segment and a second deoxyribonucleic acid segment, wherein the molecular probe has an affinity to bond to a defined nucleic acid sequence;
   supplying the sample fluid to a nanoscale deterministic lateral displacement array;
   separating, via the nanoscale deterministic lateral displacement array, the first deoxyribonucleic acid segment from the second deoxyribonucleic acid segment based on a size of the first deoxyribonucleic acid segment; and
   determining whether the first deoxyribonucleic acid segment comprises the defined nucleic acid sequence by detecting a flow path of the molecular probe in the nanoscale deterministic lateral displacement array, wherein a size of the molecular probe is less than a critical diameter of the nanoscale deterministic lateral displacement array, and wherein a size of the first deoxyribonucleic acid segment is greater than or equal to the critical diameter.

2. The method of claim 1, wherein the forming the sample fluid comprises annealing the molecular probe and the fluid to facilitate a chemical reaction between the molecular probe and one of the first deoxyribonucleic acid segment and the second deoxyribonucleic acid segment.

3. The method of claim 2, further comprising:
   detecting, by a sensor, a location of the molecular probe.

4. The method of claim 3, wherein a system operatively coupled to a processor performs the detecting based on the location.

5. The method of claim 1, wherein the first deoxyribonucleic acid segment comprises the defined nucleic acid sequence, wherein the forming the sample fluid further comprises covalently bonding the molecular probe to the first deoxyribonucleic acid segment, and wherein the separating further comprises separating the molecular probe from the second deoxyribonucleic acid segment.

6. The method of claim 1, wherein the separating further comprises separating the molecular probe from the first deoxyribonucleic acid segment.

7. The method of claim 1, wherein the first deoxyribonucleic acid segment is larger than the second deoxyribonucleic acid segment.

8. The method of claim 1, wherein the nanoscale deterministic lateral displacement array comprises a first output region and a second output region, wherein the separating comprises guiding a molecule to the first output region, wherein a molecular size of the molecule is less than a predefined threshold, wherein the separating further comprises displacing the first deoxyribonucleic acid segment to the second output region, and wherein a molecular size of the first deoxyribonucleic acid segment is greater than or equal to the predefined threshold.

9. The method of claim 8, wherein the molecule is selected from a group consisting of the second deoxyribonucleic acid segment and the molecular probe.

10. The method of claim 9, wherein the separating comprises guiding both the second deoxyribonucleic acid segment and the molecular probe to the first output region.

11. The method of claim 1, wherein the molecular probe comprises an identifier selected from a group consisting of a fluorescent tag and a magnetic bead.

12. A method, comprising:
    forming a sample fluid by annealing a fluid comprising a probe molecule, a first deoxyribonucleic acid segment, and a second deoxyribonucleic acid segment, wherein the probe molecule bonds to the first deoxyribonucleic acid segment based on the first deoxyribonucleic acid segment comprising a defined nucleic acid sequence;
    suppling the sample fluid to a nanoscale deterministic lateral displacement array;
    separating, via the nanoscale deterministic lateral displacement array, the first deoxyribonucleic acid segment from the second deoxyribonucleic acid segment based on a size of the first deoxyribonucleic acid segment; and
    determining whether the first deoxyribonucleic acid segment comprises the defined nucleic acid sequence by detecting a flow path of the probe molecule through the nanoscale deterministic lateral displacement array, wherein a size of the probe molecule is less than a critical diameter of the nanoscale deterministic lateral displacement array, and wherein a size of the first deoxyribonucleic acid segment is greater than or equal to the critical diameter.

13. The method of claim 12, wherein the first deoxyribonucleic acid segment is displaced laterally away from a flow path of the second deoxyribonucleic acid segment.

14. The method of claim 12, wherein the probe molecule covalently bonds to the defined nucleic acid sequence.

15. The method of claim 14, wherein the first deoxyribonucleic acid segment and the probe molecule are displaced laterally away from a flow path of the second deoxyribonucleic acid segment.

16. The method of claim 14, wherein the first deoxyribonucleic acid segment is displaced laterally away from a flow path of the second deoxyribonucleic acid segment and the probe molecule.

17. A method, comprising:
    forming a sample fluid by adding a molecular probe to a fluid comprising a deoxyribonucleic acid segment, wherein the molecular probe has an affinity to bond to a defined nucleic acid sequence;
    supplying the sample fluid to a nanoscale deterministic lateral displacement array;
    displacing, via nanoscale deterministic lateral displacement array comprised within a microfluidic channel, the deoxyribonucleic acid segment towards a collection region of the microfluidic channel, wherein the nanoscale deterministic lateral displacement array displaces a molecule having a size greater than a defined threshold, and wherein a size of the molecular probe is less than the defined threshold; and determining whether the deoxyribonucleic acid segment comprises the defined nucleic acid sequence by detecting a flow path of the molecular probe through the nanoscale deterministic lateral displacement array, wherein a size of the molecular probe is less than a critical diameter of the nanoscale deterministic lateral displacement array, and wherein a size of the deoxyribonucleic acid segment is greater than or equal to the critical diameter.

18. The method of claim 17, wherein the deoxyribonucleic acid segment comprises the defined nucleic acid sequence, wherein the forming the sample fluid comprises bonding the molecular probe to the deoxyribonucleic acid segment, wherein the displacing comprises displacing the molecular probe towards the collection region, and wherein the deoxyribonucleic acid segment is determined to comprise the defined nucleic acid sequence based on the flow path of the molecular probe entering the collection region.

19. The method of claim 17, wherein the displacing further comprises displacing the deoxyribonucleic acid segment from the molecular probe.

20. The method of claim 17, wherein the deoxyribonucleic acid segment is larger than the defined threshold.

* * * * *